United States Patent
Renier et al.

(10) Patent No.: US 7,125,860 B1
(45) Date of Patent: Oct. 24, 2006

(54) CROSS-LINKED DERIVATIVES OF HYALURONIC ACID

(75) Inventors: Davide Renier, Padua (IT); Vittorio Crescenzi, Rome (IT); Andrea Francescangeli, Rome (IT)

(73) Assignee: Fidia Farmaceutici S.p.A., Abano Terme (IT)

( * ) Notice: Subject to any disclaimer, the term of this patent is extended or adjusted under 35 U.S.C. 154(b) by 265 days.

(21) Appl. No.: 10/363,273

(22) PCT Filed: Aug. 31, 2001

(86) PCT No.: PCT/EP01/10063

§ 371 (c)(1), (2), (4) Date: Jun. 23, 2003

(87) PCT Pub. No.: WO02/18450

PCT Pub. Date: Mar. 7, 2002

(30) Foreign Application Priority Data

Aug. 31, 2000 (IT) .......................... PD2000A0207

(51) Int. Cl.
  *A61K 31/728* (2006.01)
  *A61K 31/715* (2006.01)
  *C08B 37/08* (2006.01)

(52) U.S. Cl. ............................ 514/54; 536/53; 536/54; 536/55.1; 536/55.2; 536/55.3; 536/123.1; 536/124

(58) Field of Classification Search ................. 514/54; 536/53, 55.1, 55.2, 55.3, 123.1, 124, 54
See application file for complete search history.

(56) References Cited

U.S. PATENT DOCUMENTS 5,874,417 A  2/1999  Prestwich et al.

FOREIGN PATENT DOCUMENTS

EP  0 466 966 A1  1/1992

OTHER PUBLICATIONS de Nooy et al., "Ionic Polysaccharide Hydrogels via the Passerini and Ugi Multicomponent Condensations: Synthesis, Behavior and Solid-State NMR Characterization," Biomacromolecules 1:259-267 (2000).
de Nooy et al., "Versatile Synthesis of Polysaccharide Hydrogels Using the Passerini and Ugi Multicomponent Condensations," Macromolecules 32:1318-1320 (1999).

*Primary Examiner*—James O. Wilson
*Assistant Examiner*—Michael C. Henry
(74) *Attorney, Agent, or Firm*—Clark & Elbing LLP

(57) ABSTRACT

The present invention describes a new class of cross-linked derivatives of partially N-deacetylated hyaluronic acid or derivatives thereof, comprising at least one repeating unit of formula (I) hereinafter depicted and a process for the preparation of said cross-linked derivatives, comprising a multicomponent condensation reaction involving the carboxy groups and the amino groups originating from a partial N-deacetylation of hyaluronic acid or derivatives, together with an aldeyde and an isocyanide. The derivatives thus obtained can be used, alone or in association with biologically and/or pharmacologically active substances, for the preparation of pharmaceutical compositions, biomaterials, surgical and healthcare articles, slow release systems and for the coating of biomedical objects.

34 Claims, No Drawings

CROSS-LINKED DERIVATIVES OF HYALURONIC ACID

CROSS REFERENCE TO RELATED APPLICATIONS

This application is a U.S. National Phase Application under 35 U.S.C. § 371 of International Application PCT/EP01/10063, filed Aug. 31, 2001, which was published in English under PCT Article 21(2) and claims priority from Italian application No. PD2000A000207, filed Aug. 31, 2000.

FIELD OF THE INVENTION

The present invention concerns a new class of cross-linked derivatives of hyaluronic acid, the process for their preparation, and their use in surgery and in the biomedical-healthcare fields.

STATE OF THE ART

Hyaluronic acid is a natural mucopolysaccharide constituted by repetitive monomeric units of N-acetyl-glucosamine and D-glucuronic acid. It is a polymer with a linear chain, the molecular weight of which may vary from 50,000 to 13,000,000 Da, depending on its source. It is present in nature in the pericellular gels, in the fundamental substance of the connective tissue of vertebrates, of which it represents one of the chief components, in the synovial fluid of the joints, in the vitreous humor, in the tissues of human umbilical cords and in cockscombs. The term HA as used herein, means both the hyaluronic acid in the acid form and the salts thereof, such as sodium, potassium, magnesium and calcium hyaluronate.

One of the chemical approaches concerning the modification of HA consists in crosslinking the chain of the polysaccharide to form a molecular network (EP 0341745 B1), the density of which depends on the degree of crosslinking that is achieved. It is also known that a lesser degree of crosslinking alters the chemical-physical characteristics of the polysaccharide, favouring the formation of viscoelastic gels or transparent mucoadhesive membranes.

Chemical modification of HA therefore enables the polysaccharide to be used for various biomedical applications, such as the prevention of surgical adhesions, by the use of gels or membranes that prevent tissue adhesion.

De Belder et al. (WO 86/00912) describe slow-degradation gels for the prevention of surgical adhesion, prepared by crosslinking the carboxy groups of HA by using bi- and poly-functional epoxides.

Other reactive agents proposed for crosslinking include 1,2,3,4-diepoxybutane in a basic solution (T. C. Laurent et al., 1964, *Acta Chem. Sca.* Vol. 18, page 274); divinyl-sulfone in an alkaline solution (E. A. Balazs et al., U.S. Pat. No. 4,582,865), and a variety of other reagent such as formaldehyde, dimethylurea, ethylene oxide, polyisocyanate (E. A. Balazs et al., UK Patent No. 8420560).

Malson et al. describe the preparation of cross-linked gels for use as substitutes for the vitreous humor (PCT Publication No. WO 86/00079).

Lastly, Della Valle et al. describe the preparation of biomaterials, such as gels, sponges and membranes for use in surgery and the biomedical-healthcare field, obtained by the reaction of auto-crosslinking between the carboxy and hydroxy groups of HA (ACP™) by the use of condensing agents such as chloro-methyl-pyridine iodide (EP 0345745 B1).

SUMMARY OF THE INVENTION

The present invention relates to a new class of cross-linked derivatives of partially N-deacetylated hyaluronic acid or derivatives thereof, comprising at least one repeating unit of formula (I) hereinafter depicted.

The present invention also provides for a process for the preparation of said cross-linked derivatives, comprising a multicomponent condensation reaction involving the carboxy groups and the amino groups originating from a partial N-deacetylation of hyaluronic acid or derivatives, together with an aldeyde and an isocyanide.

The derivatives thus obtained exhibit different chemical-physical properties according to the degree to which they are cross-linked, and can be used, alone or in association with biologically and/or pharmacologically active substances, for the preparation of pharmaceutical compositions, biomaterials, surgical and healthcare articles, slow release systems and for the coating of biomedical objects.

DETAILED DESCRIPTION OF THE INVENTION

The present invention is directed to cross-linked derivatives of partially N-deacetylated hyaluronic acid or derivatives thereof, comprising at least one repeating unit of formula (I):

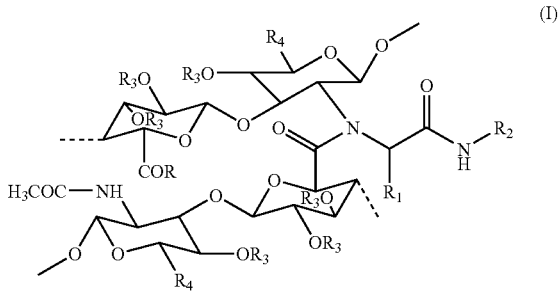

wherein $R_1$ is H or a residue C1–C20, substituted or unsubstituted, derived from an aldehyde of the aliphatic, aromatic, arylaliphatic, cycloaliphatic, heterocyclic series, provided that the said aldehyde is liquid at room temperature;

$R_2$ is a aliphatic, aromatic, arylaliphatic, cycloaliphatic or heterocyclic group, substituted or unsubstituted;

R is OH, O⁻, an alcoholic group of the aliphatic, aromatic, arylaliphatic, cycloaliphatic, heterocyclic series, or an amino group of the aliphatic, aromatic, arylaliphatic, cycloaliphatic, heterocyclic series;

the groups $R_3$, equal or different from each other, are H, $SO_3^-$, or a residue of hemiesters of succinic acid or of heavy metal salts of hemiesters of succinic acid;

and wherein the groups $R_4$, equal or different from each other, are a group COR, or a group $CH_2OR_3$, where R and $R_3$ are defined as above.

Of the hyaluronic acid derivatives that can be used to prepare the cross-linked derivatives of the invention, the following are preferred:

partial esters of hyaluronic acid containing at least one free carboxy group and the remaining carboxy groups being esterified with alcohols of the aliphatic, aromatic, arylaliphatic, cycloaliphatic and heterocyclic series, prepared as disclosed in EP 0216453 B1, which we incorporate herewith by reference;

hemiesters of succinic acid or heavy metal salts of the hemiesters of succinic acid with hyaluronic acid or with partial esters of hyaluronic acid, prepared as disclosed in WO 96/357207, which we incorporate herewith by reference;

O-sulphated hyaluronic acid and derivatives thereof, prepared as disclosed in U.S. Pat. No. 6,051,701, which we incorporate herewith by reference;

amides of hyaluronic acid or a derivative thereof with an amine of the aliphatic, aromatic, arylaliphatic, cycloaliphatic, heterocyclic series, prepared as disclosed in WO 00/01733, which we incorporate herewith by reference;

percarboxylated hyaluronic acid and derivatives thereof, prepared as disclosed in the co-pending patent application in the name of the Applicant;

hyaluronic acid salts with biologically or pharmacologically active substances;

hyaluronic acid salts with heavy metals.

According to the invention, the said heavy metals are selected from the metals of the $4^{th}$, $5^{th}$ and $6^{th}$ period of the periodic table of elements, and preferably are selected from the group consisting of silver, cobalt, iron, copper, zinc, arsenic, strontium, zirconium, antimony, gold, caesium, tungsten, selenium, platinum, gallium, ruthenium, bismuth, tin, titanium and mercury.

Of the pharmacologically active substances the following are preferred: antibiotics, anti-infective, antimicrobial, antiviral, antifungal, cytostatic, anticancer, antiinflammatory, wound healing agents, anaesthetics, cholinergic or adrenergic agonists and antagonists, antithrombotics, anticoagulants, haemostatics, fibrinolytics, and thrombolytics.

As biologically active substances should be intended for example proteins and their fragments, peptides and polynucleotides, growth factors, enzymes, vaccines and substances used in the treatment of diseases associated with genetic defects, such as those depending on enzymatic hypo- or hyper-activity due to defects of the gene encoding for a given enzyme, deforming diseases and hereditary diseases.

Amongst the cross-linked derivatives of the invention, of particular interest are those in which $R_1$ is selected from H, $CH_3$ and $CH(OH)CH_2OH$, and more preferably $R_1$ is H.

Moreover, according to a preferred embodiment of the invention, $R_2$ is selected from C1–C20 aliphatic groups, linear or branched, aromatic groups with one or more unsaturated rings having 5 to 6 members, containing or not at least one heteroatom, cycloaliphatic having 5 to 6 members and arylaliphatic groups with an aliphatic moiety C1–C20 and an aryl moiety with one or more unsaturated rings having 5 to 6 members. More preferably $R_2$ is selected from the group consisting of cyclohexyl and tert-butyl.

When not otherwise specified, the terms aliphatic, aromatic, arylaliphatic, cycloaliphatic and heterocyclic, as used herein, should be intended as follows:

"aliphatic" means acyclic or pertaining to open-chain or branched carbon compounds such as alkanes, alkenes or alkynes. Examples of an aliphatic moiety include but are not limited to C1–C20 noncyclic hydrocarbons and their isomers such as methyl, ethyl, propyl, isopropyl, n-butyl, tert-butyl, pentyl, isopentyl, neopentyl, tert-pentyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,2-ethylbutyl, 2-ethylbutyl, 1,1,2-trimethylpropyl, heptyl, octyl, nonyl, decyl, undecyl, dodecyl, tridecyl, tetradecyl, pentadecyl, hexadecyl, cetyl, heptadecyl, octadecyl, nonadecyl, stearyl, etc.

"aromatic" means an aryl moiety having one or more unsaturated rings, each ring usually having 5 to 8 members and preferably 5 to 6 members. Examples of the aromatic moiety include but are not limited to benzyl, toluyl, naphalyl, anthracenyl, phenantryl, fluorenyl, coronenyl, triphenylenyl, fluoranthenyl, benzofluoranthenyl, benzopyrenyl and pyrenyl.

"cycloaliphatic" indicates a carbon ring structure, usually having 3 to 8 members and preferably 5 to 6 members, that does not contain a resonance structure. Examples of cycloaliphatic groups include but are not limited to cycloalkanes and cycloolefins such as cyclopropyl, cyclobutyl, cyclopentyl, cyclohexyl, cycloheptyl, cyclooctyl, cyclohexenyl (tetrahydrobenzenyl), cyclohexylidenyl, and cyclooctadienyl.

"heterocyclic" relates to dissimilar atoms in a ring. A heterocyclic group is a heteroaryl group usually having a 3- to 8-membered, preferably 5- to 6-membered ring or fused ring containing at least one hetero atom (such as O, S, N, etc.) and include but are not limited to thienyl, furanyl, pyranyl, 2H-pyrrolyl, imidazolyl, pyrazolyl, pyridyl, pyrazinyl, pyrimidyl, pyridazinyl, isothiazolyl, isoxazolyl, furazanyl, benzothienyl, isobenzofuranyl, chromenyl, indolindinyl, isoindolyl, indolyl, purinyl, quinolidinyl, isoquinolyl, quinolyl, phtalazinyl, quinazolyl, carbazolyl, acridinyl, and phenanthridinyl.

"arylaliphatic" means a group having both aromatic and aliphatic substituents as defined above. Examples of arylalkyl groups include but are not limited to ethylbenzenyl, isobutylbenzeneyl, benzyl, ethylbenzyl, propylbenzyl, isopropylbenzyl, butylbenzyl, isobutylbenzyl, cyclohexylbenzyl, styrenyl, and biphenyl.

The present cross-linked derivatives can be obtained by a multicomponent condensation reaction, known in organic chemistry as "Ugi's reaction". This reaction has been described by the same author in the preparation of a network based on alginate for the immobilisation of an enzyme (Ugi et al., "Chemistry and Biochemistry of Amino Acids, Peptides and Proteins", Weinstein Ed., New York 1982, vol. 6, page 245) and has been applied in the preparation of hydrogels by De Nooy et al. (Biomacromolecules, 2000, vol. 1, No. 2, page 259).

In the context of the present invention, "Ugi's condensation" means the chemical reaction involving four molecular species belonging to the classes of carboxylic acids, primary amines, aldehydes and isocyanides.

In the following Scheme 1 the Ugi's four-component condensation is schematically reported, wherein the primary amine $R_4$—$NH_2$ condenses with the carbonylic group of the aldehyde $R_1CHO$ to give an imine (formula 1a). The protonated imine first reacts with the isocyanide $R_2$—NC yielding the compound of formula 1b, and lastly with the carboxylic function $R_3$—$COO^-$ yielding the compound of formula 1c, and then the α-(acylamine)amide of formula 1d.

Scheme 1

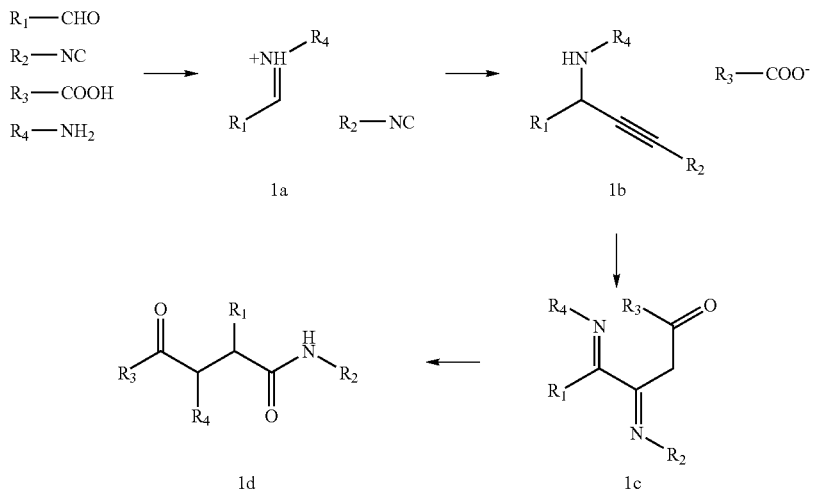

Although the Ugi's condensation is known as a synthesis procedure for the crosslinking of polymers and carboxylated polysaccharides, the inventive step that characterises the present process consists in using previously N-deacylated HA or derivatives thereof having a percentage of N-deacetylation that ranges between 1% and 50% with respect to all the N-acetylated groups present, and preferably between 5 and 30%.

According to the present invention the term "N-deacetylated HA" means the product obtained by the N-deacetylation reaction, wherein the N-acetylic groups of the N-acetylglucosaminic residue are partially substituted with a hydrogen, yielding a primary amine group.

The term "percentage of N-deacetylation", as used herein, means the quantity of N-acetylic groups of the N-acetylglucosaminic residue eliminated during the deacetylation reaction. This value is equivalent to the percentage of free amino groups available for the crosslinking reaction.

"Crosslinking reaction" means the reaction that gives rise to a covalent-type chemical bond between the hyaluronic acid chains, which is the expected outcome of Ugi's condensation. "Degree of crosslinking" means the number of condensations involved in the crosslinking reaction. The degree of cross-linking proved, surprisingly, to be equivalent to the degree of N-deacetylation, thus further supporting the evidence provided by the high specificity and chemical yield of Ugi's condensation reaction.

The process for the preparation of the present cross-linked derivatives comprises therefore the following two steps:
a) controlled N-deacetylation of hyaluronic acid or a derivative thereof to obtain the corresponding partially N-deacetylated hyaluronic acid or derivative thereof;
b) Ugi's condensation of the partially N-deacetylated hyaluronic acid or derivative thereof coming from step a) with an aldehyde and an isocyanide.

The peculiarity of the Ugi's condensation in the present process lies in the fact that of the four components involved in this reaction (a primary amine, a carboxylic acid, an aldehyde and an isocyanide), two functional groups, the primary amine and the carboxy group, belong to the hyaluronic acid or derivative thereof; of these, the carboxy function is naturally present on the D-glucuronic residue, while the amino group derives from the partial N-deacetylation of the N-acetylglucosamine residue. On the contrary, the Ugi's reaction as already described by other authors, requires the presence of a polyamine (e.g. 1,5-diaminopentane) able to act as a crosslinking agent.

The presence of the primary amino group on the HA chain leads to two important advantages: the first is the elimination of a further compound from the condensation reaction, and this undoubtedly plays an important role in the course of the degradation of the cross-linked product as it reduces the risks involved in the release of an organic amine; the second advantage is that, at the same degree of crosslinking, as two HA groups are involved in the reaction, a derivative is obtained that is characterised by a higher number of free carboxy functions that, in their turn, may be involved in other chemical modifications, such as esterification, amidation, salification with pharmacologically active molecules or with heavy metals having antibacterial, antiviral or anticancer properties, etc.

Moreover, the cross-linking reaction of the invention takes place in aqueous phase at room temperature. Another advantage is the fact that, according to the high chemical yield of Ugi's condensation reaction, the degree of crosslinking can easily be adjusted according to the percentage of N-deacetylation used (equivalent to the number of free amino groups able to intervene in the reaction).

The derivatives thus obtained present the peculiarity of absorbing water and forming hydrogels with viscoelastic characteristics depending on the degree of crosslinking that is reached. It is able to give rise to hydrogels with viscoelastic properties varying depending on the degree of crosslinking, that can be used as healthcare and surgical articles and for the preparation of pharmaceutical compositions to vehicle drugs.

According to the chemical-physical characteristics associated with the biological properties typical of the natural polysaccharide, hyaluronic acid, these cross-linked products are particularly suitable in the biomedical and healthcare field and as surgical devices for the prevention of adhesions, as fillers and as substitutes for the vitreous humor in ophthalmology or as transport systems for the controlled release of drugs.

The gels obtained at the end of the reaction have viscoelastic properties, as previously emphasised, they swell in water according to the degree of crosslinking and they are colourless and completely transparent.

Since carboxy and amino groups are involved in the condensation reaction giving rise to amidic-type covalent bonds, the gels obtained show a high level of resistance to hydrolysis (again, in relation to their degree of crosslinking), and this makes it possible to use them for therapeutic applications wherein the residence time may play a crucial role.

The cross-linked derivatives according to the present invention may be used, in association with radioactive and non-radioactive substances to be used in contrast systems, for the preparation of markers in in vivo diagnostics for the identification and treatment of tumoral or damaged tissues.

The present cross-linked derivatives may be also used in the processes of coating objects used both in medical and industrial fields, giving new biological characteristics to the surfaces of the material used as a support.

Examples of objects that can be coated are a bypass, a venous catheter, a shunt, a catheter, a guide channel, a probe, cardiac valves, artificial tendons, bone and cardiovascular replacements, contact lenses, soft tissue replacements, replacements of animal origin, blood oxygenators, artificial kidneys, hearts, pancreas and livers, blood bags, syringes, surgical instruments, filtration systems, laboratory instruments, containers for cells and tissues cultures and for the regeneration of cells and tissues, supports for peptides, proteins and antibodies.

The process of coating the surface of such objects can be performed, for example by the Plasma Coating technique, described in the Patent Application in the name of the Applicant No. WO 96/24392.

As above said, the present cross-linked derivatives can be also processed in different forms of biomaterials, such as microspheres, nanospheres, membranes, sponges, threads, films, gauzes, guide channels, hydrogels, non-woven tissues, felts, and associations thereof. Such biomaterials may comprise one or more cross-linked derivatives of the invention, optionally in association with a natural, a semisynthetic or a synthetic polymer and, optionally, further being in association with biologically or pharmacologically active substances.

Examples of natural polymers that can be used are collagen, coprecipitates of collagen, glycosaminoglycans, cellulose, polysaccharides in the form of gels such as chitin, chitosan, pectin or pectic acid, agar, agarose, xanthane, gellan, alginic acid or the alginates, polymannans or polyglycans, starch and natural gums.

Examples of semisynthetic polymers are collagen cross-linked with agents such as aldehydes or precursors of the same, dicarboxylic acids or their halides, diamine, derivatives of cellulose, hyaluronic acid, chitin or chitosan, xanthane, pectin or pectic acid, polyglycans, polymannan, agar, agarose, natural gums and glycosaminoglycans.

Synthetic polymers, for example, can be selected from the group consisting of polylactic acid, polyglycolic acid or copolymers of the same or their derivatives, polydioxane, polyphosphazenes, polysulphonic resins, polyurethanes and PTFE. Such biomaterials can be used in haemodialysis, cardiology, angiology, dermatology, ophthalmology, otorhinolaryngology, dentistry, orthopaedics, igynaecology, urology, in extracorporeal blood circulation and oxygenation, in cosmetics and in various fields of surgery, such as pelvic, abdominal, spinal, cardiac, vascular, ophthalmic, orthopaedic, otorhinolaryngological and plastic-aesthetic surgery.

Moreover, the said biomaterials can be used, in association with fibrin, and optionally with other biologically active substances, for the preparation of surgical glues.

The present biomaterials can be successfully used also as scaffolds for cells cultures, such as mesenchimal cells or mature cells to obtain connective, glandular and nerve tissue.

Preparation of a Partially N-Deacetylated HA or Derivative Thereof

Fractions of HA obtained from animal or fermentation sources, with a molecular weight of between 5,000 and 5,000,000 Da, preferably between 50,000 and 300,000 Da, or derivatives thereof, having a purity of no less than 95%, are solubilised in hydrazine or hydrazine monohydrate in a concentration of between 1 and 50 mg/ml, preferably between 5 and 25 mg/ml. The solution thus obtained is supplemented with a quantity of hydrazine sulphate of between 0.1 and 3% w/v, preferably 1%.

The reaction is carried out at a temperature within the range of 40–90° C., preferably 60° C., while being constantly stirred. The reaction time depends on the percentage of N-deacetylation that is to be obtained, and it is preferably comprised between 8 and 48 hours. Table 1 reports, as an example, the percentage of N-deacetylation for 4 HA derivatives (HADe) prepared by the Applicant, which proved to be relative to the reaction time, expressed here in hours.

TABLE 1

| Test | Time (hours) | N-deacetylation (%)* |
|---|---|---|
| HADe 1 | 8 | 5 |
| HADe 2 | 16 | 9 |
| HADe 3 | 24 | 14 |
| HADe 4 | 48 | 23 |

*the percentage of N-deacetylation is determined according to the method of J. Riesenfeld (Analy. Bioch. 1990, vol. 188, 383–389)

The reaction is then stopped by precipitation with a polar solvent, preferably ethanol. Once it has been partially vacuum-dried, the precipitate is treated with iodic acid with a molar concentration of between 0.1 and 1 M, preferably 0.5 M, and subsequently with 57% hydrogen iodide (w/v). The pH of the solution is maintained between 5–7 by adding a 10% solution (w/v) of sodium acetate.

The aqueous phase containing the modified polysaccharide is extracted by repeated treatment with ethyl ether, until the aqueous phase has been completely discoloured (it starts as an intense shade of yellow-brown). Lastly, it is precipitated with polar solvent, preferably ethanol.

The product harvested as a white precipitate is vacuum dried for at least 48–72 hours at 30° C.

In the following Scheme 2 the N-deacetylation step is illustrated:

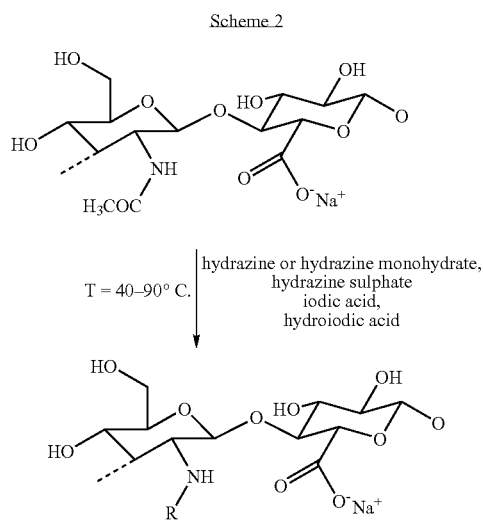

Scheme 2 wherein R is H or COCH$_3$.

Preparation of the Present Cross-Linked HA or Derivatives Thereof

The partially N-deacetylated product obtained as above described, is solubilised in water at a w/v concentration of between 1 and 10%, preferably within the range of 8–12%. The pH of the solution obtained is adjusted to between 4.5 and 5 by adding 6M HCl.

An excess (about 20–25 times the number of moles of N-deacetylated HA or derivative thereof) of an aldehyde selected from aldehydes C1–C20, substituted or unsubstituted, of the aliphatic, aromatic, arylaliphatic, cycloaliphatic, heterocyclic series, provided that the said aldehyde is liquid at room temperature; and an excess (about 80–100 times the number of moles of N-deacetylated HA or derivative thereof) of an isocyanide selected from isocyanides, substituted or unsubstituted, of the aliphatic, aromatic, arylaliphatic, cycloaliphatic or heterocyclic series, are then added.

According to a preferred embodiment of the present process, the aldehyde is selected from the group consisting of formaldehyde, acetaldehyde and glyceraldehyde, and more preferably is formaldehyde.

The isocyanide is preferably selected from between cyclohexylisocyanide and butylisocyanide, which are commercially available. However, for the purposes of the invention, it is also possible to use a series of isocyanides that are not commercially available but which can be synthesised in a laboratory (as for example described by T. Lindhorst et al. 1999, *Tetrahedron*, 55, 7411–7420).

The reaction proceeds at room temperature and under constant stirring for a period of time ranging between 20 seconds and a few minutes depending on the starting percentage of N-deacetylation.

The reaction ends with the formation of a transparent gel that tends to impede the stirring mechanism by causing friction. Table 2 reports, under the same conditions, the cross-linking reaction time expressed in seconds with regard to the percentage of N-deacetylation of the HA derivative used as an intermediate.

TABLE 2

| Test | N-deacetylation (%) | N-deacetylated HA concentration (% w/v) | Reaction time (s) |
|---|---|---|---|
| HACL 1* | 4 | 10 | 180 |
| HACL 2 | 9 | 10 | 55 |
| HACL 3 | 14 | 10 | 25 |

*HACL = cross-linked derivative of HA

Having been left to stand overnight, the gel is then transferred into a 0.1 M solution of carbonate of soda and left in these conditions for at least 16–24 hours. Lastly, it is dialysed against distilled water for at least a week.

The gel can then be lyophilised and then rehydrated in water to the desired concentration.

Moreover, the lyophilised and pulverised product can be transformed into membranes and threads by a dry extrusion process involving the use of aqueous solutions.

The same lyophilised and pulverised product can be hydrated in suitable solvents, preferably constituted by aqueous buffered solutions, together with pharmacologically active molecules (for example anti-inflammatories, antiviral agents, etc.), polypeptides, proteins and enzymes (calcitonin, RGD, etc) growth factors (BMP, NGF, OP1 etc) and vaccines.

Moreover, the present process can be applied both to the native polysaccharide itself and to derivatives of the same, thus obtaining all the cross-linked derivatives above reported. For example, it is possible to obtain molecular networks starting from hyaluronic acid, wherein part or all of the hydroxy groups have been sulphated as described in U.S. Pat. No. 6,051,701 in order to obtain a new family of derivatives to be used in the vascular and cardiovascular fields.

Moreover, before being cross-linked as described in the present invention, hyaluronic acid can be partially esterified with an alcohol of the aliphatic, aromatic, heterocyclic series, or with an alcohol constituted by a pharmacologically active ingredient that is released during scission by hydrolysis of the ester bond.

Another important application consists in using heavy metal salts belonging to the 4$^{th}$, 5$^{th}$ or 6$^{th}$ period of the periodic table, with anticancer, antimicrobial and antiviral properties. The various HA fractions, previously salified with these metals, can be cross-linked according to the present invention.

The biomaterials comprising the present cross-linked derivatives can be used, in association with biologically and/or pharmacologically active substances, as vehicling agents for the preparation of slow release pharmaceutical compositions; moreover, the present cross-linked derivatives can be used as the active ingredients, in combination with pharmaceutically acceptable excipients and/or diluents, for the preparation of pharmaceutical compositions.

Thanks to the presence of free carboxy groups in the present cross-linked derivatives, the same HA derivatives as reported above may be obtained by chemical reaction, such as esterification, amidation, salification, etc., after cross-linking.

The following examples are given to provide non-limiting illustrations of the present invention.

EXAMPLE 1

Preparation of an HA Hydrogel with a Degree of Crosslinking of 14%, Using Formaldehyde and Cyclohexylisocyanide 0.5 g of HA of extractive origin, with a molecular weight of 195,000 Da, is solubilised in 25 ml of monohydrate hydrazine, together with 0.25 g of hydrazine sulphate.

The solution is agitated for 24 hours at 60° C., after which the reaction is stopped by adding 50 ml of ethanol. The precipitate in the form of a hydrogel is washed and dried at room temperature overnight.

The intermediate product is then redissolved in 25 ml of distilled water and 10 ml of a solution of sodium acetate, 10% w/v, after which 15 ml of a 0.5 M solution of iodic acid is added. Thirty minutes later, 2.5 ml of 57% hydrogen iodide is added. During this last operation, the temperature is maintained at 0° C. by means of an ice bath.

The aqueous solution, of a strong brown colour, is treated with liquid—liquid extraction at least five times with 25 ml of ethyl ether. Lastly, after adjusting the pH of the discoloured solution containing the modified polysaccharide to between 6.5 to 7 with NaOH 1 N, it is precipitated with 100 ml of ethanol. The precipitate, which is white, is washed with ethanol and vacuum-dried for at least 48 hours.

The degree of de-acetylation is 14%.

0.4 g of the partially de-N-acetylated derivative is dissolved in 4 ml of distilled water and the pH is adjusted to between 4.5 and 5 by adding a few drops of 6M HCl. Lastly, it is supplemented with 100 µl of formaldehyde and 100 µl of cyclohexyl isocyanide.

This is agitated for about 1 minute, after which a slightly opaque, three-dimensional hydrogel can be seen to form. The solution is then left to stand for at least 12 hours.

The hydrogel is then transferred to a 0.1 N solution of sodium carbonate and then left for at least 6 hours in order to hydrolyse all the esters formed as a secondary product of Ugi's reaction. Lastly, the hydrogel is dialysed against at least 200 volumes of distilled water.

The transparent hydrogel presents a degree of swelling within the range of 10–20 (expressed as the wet weight/dry weight ratio).

EXAMPLE 2

Preparation of an HA Hydrogel with a Degree of Crosslinking of 9%, Using Formaldehyde and Cyclohexylisocyanide 0.5 g of HA of extractive origin with a molecular weight of 210,000 Da is solubilised in 25 ml of hydrazine monohydrate, together with 0.25 g of hydrazine sulphate. The solution is agitated for 16 hours at 60° C., after which the reaction is stopped by adding 50 ml of ethanol. The precipitate, in the form of a hydrogel, is washed and dried at room temperature overnight.

The intermediate product is then redissolved in 25 ml of distilled water and 10 ml of a 10% sodium acetate solution w/v, and then 15 ml of a 0.5 M solution of iodic acid is added. Thirty minutes later, 2.5 ml of 57% hydrogen iodide is added. During this last operation, the temperature is maintained at 0° C. with an ice bath.

The aqueous solution, which is a strong brown colour, is treated by liquid—liquid extraction at least five times with 25 ml of ethyl ether. Lastly, the pH of the discoloured solution containing the modified polysaccharide is adjusted to between 6.5 and 7 with NaOH 1 N, and then it is precipitated with 100 ml of ethanol. The white-coloured precipitate is washed with ethanol and vacuum-dried for at least 48 hours.

The degree of de-acetylation is 9%.

0.45 g of the partially de-N-acetylated derivative is dissolved in 4.5 ml of distilled waster and the pH is adjusted to between 4.5 and 5 by adding a few drops of HCl 6M. 70 µl of formaldehyde and 70 µl of cyclohexylisocyanide are then added.

This is stirred for about 3 minutes (even though a hydrogel can be seen to be forming after only one minute) and then it is left to stand for at least 12 hours.

The hydrogel is then transferred to a 0.1 N solution of sodium carbonate and then left to stand for at least 6 hours in order to hydrolyse all the esters formed as a secondary product of Ugi's reaction. Lastly, the hydrogel is dialysed against at least 200 volumes of distilled water.

The transparent hydrogel presents a degree of swelling of 20–50 (wet weight/dry weight ratio).

EXAMPLE 3

Preparation of an HA Hydrogel with a Degree of Crosslinking of 23%, Using Acetaldehyde and Butylisocyanide 1.0 g of HA of extractive origin with a molecular weight of 210,000 Da is solubilised in 100 ml of hydrazine monohydrate, together with 1.0 g of hydrazine sulphate. The solution is stirred for 48 hours at 60° C., after which the reaction is stopped by adding 150 ml of ethanol. The precipitate, in the form of a hydrogel, is washed and dried at room temperature overnight.

The intermediate product is then redissolved in 100 ml of distilled water and 20 ml of a 10% sodium acetate solution w/v, and then 30 ml of a 0.5 M solution of iodic acid is added. Thirty minutes later, 5 ml of 57% hydrogen iodide is added. During this last operation, the temperature is maintained at 0° C. with an ice bath.

The aqueous solution, which is a strong brown colour, is treated by liquid—liquid extraction at least five times with 50 ml of ethyl ether. Lastly, the pH of the discoloured solution containing the modified polysaccharide is adjusted to between 6.5 and 7 with NaOH 1 N, and then the solution is precipitated with 200 ml of ethanol. The white-coloured precipitate is washed with ethanol and vacuum-dried for at least 48 hours.

The degree of de-acetylation is 23%.

0.9 g of the partially de-N-acetylated derivative is dissolved in 4.5 ml of distilled waster and the pH is adjusted to between 4.5 and 5 by adding a few drops of HCl 6 M. 300 µl of acetaldehyde and 250 µl of butylisocyanide are then added.

This is agitated for about 30 seconds (even though a hydrogel can be seen to be forming after only one minute) and then it is left to stand for at least 12 hours.

The hydrogel is then transferred to a 0.1 N solution of sodium carbonate and then left to stand for at least 6 hours in order to hydrolyse all the esters formed as a secondary product of Ugi's reaction. Lastly, the hydrogel is dialysed against at least 200 volumes of distilled water.

The transparent hydrogel presents a degree of swelling of between 4–8 (wet weight/dry weight ratio).

EXAMPLE 4

Preparation of a Pharmaceutical Composition Constituted by Bone Growth Factor BMP Incorporated in a Hydrogel with a Degree of Crosslinking of 14%

The hydrogel obtained as per example 1 is lyophilised and pulverised.

50 µg of BMP is added to the powder, after which 5 ml of 20 mM phosphate buffer solution at pH 6.8 is added, having previously been filtered through 0.22µ. The hydrogel is left to hydrate for at least 12 hours and then it is poured into a vial, ready to be used in the orthopaedic field.

What is claimed is:

1. A cross-linked derivative of partially N-deacetylated hyaluronic acid or derivatives thereof, comprising at least one repeating unit of formula (I):

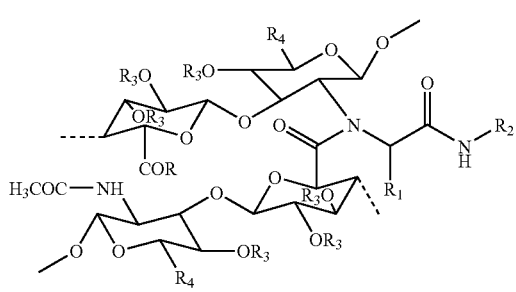

wherein $R_1$ is H or a residue C1–C20, substituted or unsubstituted, derived from an aliphatic, aromatic, arylaliphatic, cycloaliphatic, or heterocyclic aldehyde, provided that the said aldehyde is liquid at room temperature;

$R_2$ is an aliphatic, aromatic, arylaliphatic, cycloaliphatic, or heterocyclic group, substituted or unsubstituted;

R is OH, O$^-$, an aliphatic, aromatic, arylaliphatic, cycloaliphatic, or heterocyclic alcoholic group, or an aliphatic, aromatic, arylaliphatic, cycloaliphatic, or heterocyclic amino group;

the groups $R_3$, equal or different from each other, are H, $SO_3^-$, or a residue of hemiesters of succinic acid or of heavy metal salts of hemiesters of succinic acid;

the groups $R_4$, equal or different from each other, are a percarboxylic group, or a group $CH_2OR_3$; and the said hyaluronic acid derivatives are selected from the group consisting of:

partial esters of hyaluronic acid esterified with aliphatic, aromatic, arylaliphatic, cycloaliphatic, or heterocyclic alcohols;

hemiesters of succinic acid or heavy metal salts of the hemiesters of succinic acid with hyaluronic acid or with partial esters of hyaluronic acid;

O-sulphated hyaluronic acid and derivatives thereof;

amides of hyaluronic acid or a derivative thereof with an aliphatic, aromatic, arylaliphatic, cycloaliphatic, or heterocyclic amine;

percarboxylated hyaluronic acid and derivatives thereof; and hyaluronic acid salts with heavy metals.

2. Cross-linked derivatives according to claim 1, wherein $R_1$ is selected from H, $CH_3$ and $CH(OH)CH_2OH$.

3. Cross-linked derivatives according to claim 1, wherein $R_1$ is H.

4. Cross-linked derivatives according to claim 1, wherein $R_2$ is selected from C1–C20 aliphatic groups, linear or branched, aromatic groups with one or more unsaturated rings having 5 to 6 members, containing or not containing at least one heteroatom, cycloaliphatic groups having 5 to 6 members and arylaliphatic groups with an aliphatic moiety C1–C20 and an aryl moiety with one or more unsaturated rings having 5 to 6 members.

5. Cross-linked derivatives according to claim 1, wherein $R_2$ is selected from consisting of cyclohexyl and t-butyl.

6. Cross-linked derivatives according to claim 1, wherein the said partially N-deacetylated hyaluronic acid or partially N-deacetylated hyaluronic acid derivatives have a N-deacetylation percentage ranging between 1 and 50%.

7. Cross-linked derivatives according to claim 6, wherein the said N-deacetylation percentage is between 5 and 30%.

8. Cross-linked derivatives according to claim 1, having a degree of crosslinking comprised between 1 and 50%.

9. Cross-linked derivatives according to claim 8, wherein the said crosslinking degree is comprised between 5 and 30%.

10. Cross-linked derivatives according to claim 1, alone or in a composition in combination with biologically active substances selected from the group consisting of proteins, peptides, polynucleotides, growth factors, enzymes, vaccines, or pharmacologically active substances selected from the group consisting of antibiotics, anti-infective, antimicrobial, antiviral, antifungal, cytostatic, anticancer, anti-inflammatory, wound healing agents, anaesthetics, cholinergic or adrenergic agonists and antagonists, antithrombotics, anticoagulants, haemostatics, fibrinolytics, and thrombolytics.

11. Cross-linked derivatives according to claim 1, wherein the said heavy metals are selected from the metals of the $4^{th}$, $5^{th}$ and $6^{th}$ period of the periodic table of elements.

12. Cross-linked derivatives according to claim 11, wherein the said heavy metals are selected from the group consisting of silver, cobalt, iron, copper, zinc, arsenic, strontium, zirconium, antimony, gold, caesium, tungsten, selenium, platinum, gallium, ruthenium, bismuth, tin, titanium and mercury.

13. A biomaterial comprising at least a cross-linked derivative of partially N-deacetylated hyaluronic acid or derivatives thereof as claimed in claim 1, alone or in combination with a natural, a semisynthetic or a synthetic polymer.

14. Biomaterial according to claim 13, wherein the said natural polymer is selected from the group consisting of collagen, coprecipitates of collagen, glycosaminoglycans, cellulose, polysaccharides in the form of gels such as chitin, chitosan, pectin or pectic acid, agar, agarose, xanthane, gellan, alginic acid or the alginates, polymannans or polyglycans, starch and natural gums.

15. Biomaterial according to claim 13, wherein the said semisynthetic polymer is selected from the group consisting of collagen cross-linked with aldehydes, dicarboxylic acids or their halides, diamine, derivatives of cellulose, hyaluronic acid, chitin or chitosan, xanthane, pectin or pectic acid, polyglycans, polymannan, agar, agarose, natural gums, and glycosaminoglycans.

16. Biomaterial according to claim 13, wherein the said synthetic polymer is selected from the group consisting of polylactic acid, polyglycolic acid or copolymers of the same or their derivatives, polydioxane, polyphosphazenes, polysulphonic resins, polyurethanes, and PTFE.

17. Biomaterial according to claim 13, in combination which biomaterial is a surgical glue.

18. Biomaterial according to claim 13, which is a healthcare or surgical article.

19. Biomaterial according to claim 18, wherein the said healthcare or surgical article is selected from the group consisting of microspheres, nanospheres, membranes, sponges, threads, films, gauzes, guide channels, hydrogels, non-woven tissues, felts, and associations thereof.

20. Biomaterial according to claim 13, which is a scaffold for cell cultures.

21. Biomaterial according to claim 13, for the preparation of scaffolds for cell cultures.

22. Biomaterial according to claim 13, as vehicling agent for the preparation of slow release pharmaceutical compositions.

23. A pharmaceutical composition comprising as the active agent at least one cross-linked derivative of partially N-deacetylated hyaluronic acid or derivatives thereof as claimed in claim 1, in combination with pharmaceutically acceptable excipients and/or diluents.

24. Diagnostic agents comprising at least one cross-linked derivative of partially N-deacetylated hyaluronic acid or derivatives thereof as claimed in claim 1, in combination with radioactive and non-radioactive substances to be used in contrast systems, for the preparation of markers in in vivo diagnostics for the identification and treatment of tumoral or damaged tissues.

25. A biomedical object coated with the cross-linked derivative of partially N-deacetylated hyaluronic acid or derivatives thereof as claimed in claim 1, wherein the said biomedical object is selected from the group consisting of a bypass, a venous catheter, a shunt, a catheter, a guide channel, a probe, cardiac valves, artificial tendons, bone and cardiovascular replacements, contact lenses, soft tissue replacements, replacements of animal origin, blood oxygenators, artificial kidneys, hearts, pancreas and livers, blood bags, syringes, surgical instruments, filtration systems, laboratory instruments, containers for cells and tissues cultures and for the regeneration of cells and tissues, supports for peptides, proteins and antibodies.

26. Healthcare and surgical articles comprising the cross-linked derivatives of partially N-deacetylated hyaluronic acid or derivatives thereof as claimed in claim 1, wherein the said healthcare or surgical articles are selected from the group consisting of microspheres, nanospheres, membranes, sponges, threads, films, gauzes, guide channels, hydrogels, non-woven tissues, felts, and associations thereof.

27. Process for the preparation of cross-linked derivatives of partially N-deacetylated hyaluronic acid or derivatives thereof as claimed in claim 1, comprising the following steps:
   a) controlled N-deacetylation of hyaluronic acid or a derivative thereof to obtain the corresponding partially N-deacetylated hyaluronic acid or derivative thereof;
   b) Ugi's condensation of the partially N-deacetylated hyaluronic acid or derivative thereof coming from step a) with an aldehyde and an isocyanide.

28. Process according to claim 27, wherein the partial N-deacetylation in step a) is carried out by using hydrazine or hydrazine monohydrate, then adding hydrazine sulphate.

29. Process according to claim 27, wherein the said step a) is carried out at a temperature comprised between 40 and 90° C.

30. Process according to claim 29, wherein the step a) is carried out at a temperature of 60° C.

31. Process according to claim 27, wherein the reaction time in step a) is comprised between 8 and 48 hours.

32. Process according to claim 27, wherein the said step b) is carried out at room temperature by adding to a water solution of the partially N-deacetylated hyaluronic acid or derivative thereof coming from step a) an excess of an aliphatic, aromatic, arylaliphatic, cycloaliphatic, or heterocyclic aldehyde selected from aldehydes C1–C20, substituted or unsubstituted, provided that the said aldehyde is liquid at room temperature; and an excess of an isocyanide selected from aliphatic, aromatic, arylaliphatic, cycloaliphatic, and heterocyclic isocyanides, substituted or unsubstituted.

33. Process according to claim 32, wherein the said aldehyde is selected from formaldehyde, acetaldehyde and glyceraldehyde, and the said isocyanide is selected from cyclohexyl isocyanide and tert-butyl isocyanide.

34. Process according to claim 32, wherein the said aldehyde is formaldehyde.

* * * * *

UNITED STATES PATENT AND TRADEMARK OFFICE
CERTIFICATE OF CORRECTION

PATENT NO. : 7,125,860 B1  
APPLICATION NO. : 10/363273  
DATED : October 24, 2006  
INVENTOR(S) : Renier et al.

Page 1 of 1

It is certified that error appears in the above-identified patent and that said Letters Patent is hereby corrected as shown below:

On the Title Page (57) in the ABSTRACT, line 9, replace "aldeyde" with --aldehyde--

Column 1, Line 58, replace "reagent" with --reagents--.

Column 2, Line 52, replace "a" with --an--.

Column 3, Line 36, replace "anaesthetics" with --anesthetics--.

Column 8,
    Line 1, replace "haemodialysis" with --hemodialysis--;
    Line 14, replace "mesenchimal" with --mesenchymal--.

Column 12, Line 53, replace "waster" with --water--.

Signed and Sealed this

First Day of May, 2007

JON W. DUDAS
*Director of the United States Patent and Trademark Office*